United States Patent
Keipert et al.

(10) Patent No.: US 6,679,859 B1
(45) Date of Patent: Jan. 20, 2004

(54) AMELIORATION OF ISCHEMIC DAMAGE USING SYNTHETIC OXYGEN CARRIERS

(75) Inventors: Peter E. Keipert, San Diego, CA (US); N. Simon Faithfull, San Diego, CA (US); Stephen F. Flaim, San Diego, CA (US); Gwen H. Rosenberg, Rancho Santa Fe, CA (US)

(73) Assignee: Alliance Pharmaceutical Corp., San Diego, CA (US)

( * ) Notice: Subject to any disclaimer, the term of this patent is extended or adjusted under 35 U.S.C. 154(b) by 0 days.

(21) Appl. No.: 09/530,075

(22) PCT Filed: Oct. 23, 1998

(86) PCT No.: PCT/US98/22491

§ 371 (c)(1),
(2), (4) Date: Jul. 31, 2000

(87) PCT Pub. No.: WO99/21541

PCT Pub. Date: May 6, 1999

Related U.S. Application Data

(60) Provisional application No. 60/063,502, filed on Oct. 24, 1997.

(51) Int. Cl.$^7$ ............................................. A61K 31/02
(52) U.S. Cl. ....................................................... 604/28
(58) Field of Search ............................................ 604/28

(56) References Cited

U.S. PATENT DOCUMENTS

| | | | |
|---|---|---|---|
| 3,937,821 A | | 2/1976 | Irikura et al. |
| 3,962,439 A | | 6/1976 | Yokoyama et al. |
| 4,173,654 A | | 11/1979 | Scherer |
| 4,186,253 A | | 1/1980 | Yokoyama et al. |
| 4,378,797 A | * | 4/1983 | Osterholm .................... 604/24 |
| 4,397,870 A | | 8/1983 | Sloviter |
| 4,423,077 A | | 12/1983 | Sloviter |
| 5,085,630 A | | 2/1992 | Osterholm et al. |
| 5,114,932 A | | 5/1992 | Runge |
| 5,344,393 A | | 9/1994 | Roth et al. |
| 5,451,205 A | | 9/1995 | Roth et al. |
| 5,723,496 A | * | 3/1998 | Nakada ....................... 514/634 |
| 5,733,871 A | | 3/1998 | Alps et al. |
| 6,044,845 A | * | 4/2000 | Lewis ......................... 128/898 |

FOREIGN PATENT DOCUMENTS

| | | |
|---|---|---|
| EP | 0037992 | 10/1981 |
| EP | 0088954 | 9/1983 |
| WO | 9210221 | 6/1992 |
| WO | 9640097 | 12/1996 |

OTHER PUBLICATIONS

Aronowski et al. "Combined Neuroprotection and Reperfusion Therapy for Stroke, Effect of Lubeluzole and Diaspirin Cross–Linked Hemoglobin in Experimental Focal Ischemia" Stroke 27(9): 1571–1577 (Sep. 1996).

Bielenberg et al. "Effects of Calcium Entry Blocker Emopamil on Postischemic Energy Metabolism of the Isolated Perfused Rat Brain" J. of Cerebral Blood Flow & Metabolism 7(4): 489–496 (1987).

Bishopp, Frances. "Interneuron's Citicoline Works for Moderate to Severe Stroke" Bioworld Today p. 3 (Thursday, Jul. 17, 1997).

Cochran et al. "Perfluorocarbon Emulsion in the Cardiopulmonary Bypass Prime Reduces Neurologic Injury" Ann Thorac Surg 63: 1326–1332 (1997).

Kagawa et al. "The Protective Effect of Mannitol and Perfluorochemicals on Hemorrhagic Infarction: An Experimental Study" Surgical Neurology 17(1): 66–70 (Jan. 1982).

Mizoi et al. "Experimental Study of New Cerebral Protective Substances—Functional Recovery of Severe, Incomplete Ischaemic Brain Lesions Pretreated with Mannitol and Fluorocarbon Emulsion" Acta Neurochirugica 56: 157–166 (1981).

Naruse et al. "Measurements of in vivo Energy Metabolism in Experimental Cerebral Ischaemia Using $^{31}$P–NMR for the Evaluation of Protective Effects of Perfluorochemicals and Glycerol" Neurological Research 6: 169–175 (Dec. 1984).

Pereira et al. "Effect of Treatment with Fluosol and Mannitol During Temporary Middle Cerebral Artery Occlusion in Cats" Neurosurgery 23(2): 139–142 (1988).

Suzuki et al. "A New Therapeutic Method for Acute Brain Infarction: Revascularization Following the Administration of Mannitol and Perluorochemicals–A Preliminary Report" Surgical Neurology 17(5): 325–332 (May 1982).

Suzuki et al. "The Protective Effect of Combined Administration of Anti–Oxidants and Perfluorochemicals on Cerebral Ischemia" Stroke 15(4): 672–679 (Jul.–Aug. 1984).

Symons et al. "Purflubron Emulsion Increase Tolerance . . . " Document XP–002104378, Cardiovascular Research Alliance Pharmaceutical Corp., 1995, FASEB Journal vol. 9 No.3 PDA622.

Hale et al. "Effect of Two Perfluorocarbon Emulsions" Basic. Res. Cardiol. 1995 90(5) 404–9 Coden: BRCA37.

Musca et al. "Perfluorocarbon Supplementation" Surgery, 87 1996 ISSN 0039–6060.

\* cited by examiner

*Primary Examiner*—J. Casimer Jacyna

(57) ABSTRACT

A method of ameliorating tissue damage resulting from hypoxia or ischemia by administering systemically a synthetic oxygen carrier to an individual having or suspected of having blood vessel obstruction is disclosed. A synthetic oxygen carrier in a physiologically acceptable vehicle, wherein the synthetic oxygen carrier comprises submicron sized particles capable of passing through emboli-obstructed blood vessels is also disclosed.

12 Claims, No Drawings

AMELIORATION OF ISCHEMIC DAMAGE USING SYNTHETIC OXYGEN CARRIERS

This application claims benefit of provisional application No. 60/063,502 filed Oct. 24, 1997.

FIELD OF THE INVENTION

This invention relates to a method of protecting living tissue from damage caused by hypoxic or ischemic conditions such as those resulting from acute vascular occlusions. More particularly, the present invention relates to the use of synthetic oxygen carriers, including perfluorocarbon-based emulsions, to carry gases to hypoxic or ischemic living tissue, and thereby ameliorate damage.

BACKGROUND OF THE INVENTION

Normal animal physiology requires efficient delivery of oxygen to living cells and tissues and efficient removal of carbon dioxide and other waste products of metabolism. In mammals, this is generally accomplished by gas exchange mediated by hemoglobin-containing red blood cells, and is primarily accomplished by red blood cells flowing through capillaries. When capillaries or larger arteries become occluded, such as by vessel constriction or solid emboli that block or partially block the blood vessels, the oxygen supply becomes compromised for tissues that depend on those vessels for oxygen. Tissue hypoxia results from failure to transport sufficient oxygen, often due to inadequate blood flow i.e. ischemia. Hypoxia can result from internal hemorrhage (e.g., intracerebral hemorrhage producing cerebral hypoxia), anemia or trauma. Ischemia is a deficiency of blood supply to the tissue due to functional constriction or actual obstruction of a blood vessel. For example, myocardial ischemia is a deficiency of blood supply to heart muscle due to obstruction or constriction of the coronary arteries. If ischemia continues for more than a few seconds, tissue damage can result from a complex series of biochemical events associated with the ischemia-induced tissue hypoxia.

Hypoxic or ischemic conditions produced by emboli can result in tissue damage that is particularly debilitating if the damaged tissue is heart tissue or neural tissue of the central nervous system (CNS). The two most serious consequences of emboli are heart attack (acute myocardial infarct or AMI), resulting from cardiac muscle ischemia, and stroke, resulting from brain tissue ischemia. Ischemia which does not lead to AMI or stroke can, nonetheless, produce serious symptoms in the individual such as chest pains (angina pectoris), partial paralysis, confusion, disorientation and/or memory loss.

Individuals with vascular disease, particularly atherosclerosis, are particularly at risk for developing emboli that can result in AMI or stroke. Ischemic heart disease affects millions of people worldwide, often leading to sudden death by AMI. Ischemia can result when solid emboli produced from portions of plaque that dislodge and move through the circulatory system lodge in a capillary or attach to another plaque deposit in a blood vessel, thus fully or partially occluding the vessel or capillary. Atheromatous plaque particles can also be generated during vascular and cardiac surgery procedures (e.g. cannulation, clamping) that manipulate or disturb any atherosclerotic blood vessels (e.g., carotids, coronaries, aorta, femoral or popliteal vessels).

Present day treatment of occlusions generally involves bypassing the blocked vessel, or removing and/or dissolving emboli using mechanical means and/or thrombolytic enzymes. For example, treatment of intracoronary thrombotic events such as myocardial infarcts usually involves one or a combination of treatments. These include coronary bypass surgery, percutaneous coronary angioplasty (PTCA) and systemic administration of thrombolytic agents, such as tissue plasminogen activator (tPA) or streptokinase. Although such treatments often successfully relieve the hypoxic or ischemic condition, significant damage to the tissue in the hypoxic zone can occur before treatment is completed.

Synthetic oxygen carriers, often referred to as "blood substitutes" have been shown to augment delivery of oxygen through the circulatory system when red blood cells (i.e., hemoglobin) are partially depleted, such as during surgery, or resulting from injury with bleeding or hemorrhagic disorders. Similarly, synthetic oxygen carriers can be used to treat conditions where the red blood cells are partially non-functional, as may occur in patients with certain genetic disorders, or patients undergoing hypothermic procedures such as cardiopulmonary bypass or circulatory arrest. Such oxygen carriers or blood substitutes are disclosed in U.S. Pat. No. 5,344,393 and U.S. Pat. No. 5,451,205. Other blood substitutes are known as disclosed in U.S. Pat. No. 5,114,932, U.S. Pat. No. 4,423,077, U.S. Pat. No. 4,397,870, U.S. Pat. No. 4,186,253, U.S. Pat. No. 4,173,654, U.S. Pat. No. 4,423,077, U.S. Pat. No. 3,962,439 and U.S. Pat. No. 3,937,821. Perfluorocarbon emulsions, such as FLUO-SOL™ (Green Cross Corporation, Japan) and OXYGENT™ (perflubron-based emulsion) (Alliance Pharmaceutical Corp., San Diego, USA), are known to be efficient synthetic oxygen carriers that are generally well tolerated in vivo by humans. Synthetic oxygen carriers comprising hemoglobin, which can be derived from human, animal, or recombinant sources, is also known in the art Given the excellent oxygen dissolving characteristics and biocompatibility of perfluorochemicals, previous efforts have led to their use in neurologic ischemia. For example, one system includes perfluorocarbon in a nutrient emulsion or "synthetic cerebrospinal fluid" to treat CNS hypoxic-ischemic conditions (U.S. Pat. No. 4,445,514). In this case the oxygenated emulsion is administered directly into the cerebrospinal fluid and artificially circulated through extracorporeal means.

Perfluorocarbon emulsions have also been used in an experimental animal model of partial brain stem ischemia and shown to enhance recovery of brain stem function following reperfusion (Guo et al., *Neurosurgery* 36(2): 350–357, 1995).

Perfluorocarbons and blood substitutes have also been used for drug delivery. For example, infusions of a neuroprotectant and a perfluorochemical emulsion have been disclosed as a treatment for conditions involving cerebral hypoxia (PCT International Application No. WO 97/15306).

SUMMARY OF THE INVENTION

According to the invention, there is provided a method of preventing or treating tissue hypoxia or ischemia, including the step of administering systemically a synthetic oxygen carrier to an individual having or suspected of having blood vessel obstruction. Preferably, the invention may be used to provide neuroprotection or retard neurodegeneration in a patient in need thereof through a reduction in the adverse effects of cerebral ischemic hypoxia. Other preferred embodiments comprise the use of synthetic oxygen carriers in chronic or long-term therapeutic regimens for the reduction or treatment of ischemic or hypoxic associated effects. Another embodiment comprises the use of perfluorochemical-based formulations to reduce the inflammatory process triggered locally by the ischemic insult and related tissue hypoxia. In selected embodiments, the oxygen carrier is administered by intravenous injection or infusion. Preferably, the synthetic oxygen carrier is a perfluarocarbon emulsion, crystalloid blood substitute, a colloid blood substitute, or combinations thereof.

As such, in a broad sense the present invention comprises the use of a synthetic oxygen carrier in the manufacture of an oxygen carrying medicament for the treatment of tissue hypoxia due to ischemia or acute anemia, wherein said oxygen carrying medicament is administered systemically to an individual having or suspected of having blood vessel obstruction caused by solid emboli, or temporary clamping of vessels during surgery.

Particularly preferred embodiments of the invention comprise the use of synthetic oxygen carriers which are fluorocarbon-in-water emulsions comprising a discontinuous fluorocarbon phase and a continuous aqueous phase. In another embodiment, the fluorocarbon-in-water emulsion includes a perfluorocarbon phase and an aqueous phase. In another embodiment, the fluorocarbon emulsion also includes an emulsifying agent or dispersant, osmotic agent, buffer, electrolyte or combinations thereof.

Generally it will be appreciated that the term "fluorocarbon" is used in a broad sense and comprises any highly fluorinated compound such as a linear, branched, cyclic, saturated or unsaturated fluorinated hydrocarbon, optionally containing at least one heteroatom and/or bromine or chlorine atom, wherein at least 30% of the hydrogen atoms of said hydrocarbon compound have been replaced by fluorine atoms. Particularly preferred embodiments comprise perfluorocarbons. Other embodiments comprise fluorocarbon emulsions including bis(F-alkyl) ethanes, cyclic fluorocarbons, perfluorinated amines, brominated perfluorocarbons, chlorinated fluorocarbons, perfluoroalkylated ethers, perfluoroalkylated polyethers or mixtures thereof that are dispersed in an aqueous phase. Fluorocarbons compatible with the present invention are generally selected for beneficial physical characteristics such as low toxicity, low surface tension, high spreading coefficient and the ability to transport gases.

Hemoglobin compositions contemplated for use in the present invention are well known. These compositions may be comprised of stroma-free, intramolecularly cross-linked, conjugated, polymerized, or recombinant hemoglobin or combinations thereof. Such compositions are disclosed, for example, in the following U.S. Patents, which are hereby incorporated by reference: U.S. Pat. Nos. 4,911,929; 4,861,867; 4,857,636; 4,777,244; 4,698,387; 4,600,531; 4,526,715; 4,473,494; and 4,301,144.

In yet another aspect, the present invention provides methods for delivering a bioactive agent to a patient using the disclosed oxygen carriers. As used herein, the term bioactive agent is defined to mean any pharmaceutical compound or composition, including diagnostic and therapeutic agents or drugs as well as physiologically acceptable gases such as oxygen or nitric oxide, which may be administered to an animal to treat a disorder or disease. Specific bioactive agents or drugs compatible with the present invention include, but are not limited to, antibiotics, antivirals, anti-inflammatories, antineoplastics, intravenous anesthetics, volatile anesthetics, enzymes, cardiovascular agents, polynucleotides, genetic material, viral vectors, immunoactive agents, imaging agents, immunosuppressive agents, peptides, proteins and combinations thereof. Preferably, the incorporated drug is a drug that promotes dissolving emboli, or a neuroprotective compound. In a selected embodiment, the neuroprotective compound is a neuropeptide, a nerve growth factor or 2-aminobenzothiazole derivative.

Accordingly, in preferred embodiments the invention provides for the use of a synthetic oxygen carrier in the manufacture of an oxygen carrying medicament for providing neuroprotection or retarding neurodegeneration through a reduction in effects associated with cerebral ischemia or hypoxia wherein said oxygen carrying medicament is administered systemically to a patient in need thereof.

More broadly, the present invention provides for the delivery of bioactive agents using emulsified medicaments capable of carrying oxygen. That is, embodiments of the present invention comprise the use of a fluorocarbon in the manufacture of an oxygen carrying emulsified medicament for the delivery of a bioactive agent wherein said emulsified medicament comprises an aqueous continuous phase, a nonaqueous dispersed phase, an emulsifying agent and a bioactive agent and wherein said emulsified medicament is administered to a patient in need thereof.

Consistent with the teachings herein the oxygen carrier may be administered either prophylactically to prevent the ischemia-induced tissue hypoxia, or as a treatment of therapy for symptoms associated with ischemia, whereas in other embodiments the administration step is performed after the ischemic event to correct symptoms associated with ischemia or hypoxia. The administration step may be performed prior to a surgical procedure to protect against emboli which will cause ischemia, or during the surgical procedure, or within 24 hours or several days after a surgical procedure to treat tissues at risk of hypoxia to emboli or other ischemic events.

As indicated above, other embodiments of the invention comprise the chronic or long term administration of oxygen carriers to reduce the deleterious effects of ischemic or hypoxia. Such therapeutic regimens may involve the low dose administration of the selected oxygen carrier for a period of weeks or even months. The actual administration of the oxygen carrier may preferably comprise discrete introductions on a periodic basis (i.e. once a day or once a week) or a constant slow infusion of the oxygen carrier using techniques well known in the art. In these embodiments, the oxygen carrier may further comprise an additional bioactive agent. It will be appreciated that such regimens may be particularly useful for ameliorating symptoms associated with chronic neurodegenerative conditions such as Alzheimer's disease, Parkinson's disease or epilepsy. Of course, it will further be appreciated that the long term administration of oxygen carriers may be used to treat non-neuronal conditions.

Accordingly, preferred embodiments of the invention provide for use of a synthetic oxygen carrier in the manufacture of an oxygen carrying medicament for the treatment of a chronic or long term hypoxic or ischemic condition in a patient in need thereof wherein said oxygen carrying medicament is administered periodically, intermittently or continuously to said patient for a treatment period greater than one week.

In another embodiment, the method includes administering a volume of an intravenous fluid including the synthetic oxygen carrier, wherein the synthetic oxygen carrier is at least about equal to 0.1% of the individual's normal blood volume. In other embodiments, the volume of an intravenous fluid including the synthetic oxygen carrier is equal to about 1% to about 20%, or 30% of the individual's normal blood volume.

According to another aspect of the invention, there is provided a composition including a synthetic oxygen carrier in a physiologically acceptable carrier, wherein the synthetic oxygen carrier includes submicron-sized particles capable of passing through emboli-obstructed blood vessels. In one embodiment, the synthetic oxygen carrier is a fluorocarbon-in-water emulsion of a discontinuous fluorocarbon phase and a continuous aqueous phase, wherein the fluorocarbon phase includes submicron sized particles. In another embodiment, the fluorocarbon-in-water emulsion also includes an emulsifying agent, osmotic agent, buffer, electrolyte, therapeutic drug or combinations thereof. Particularly preferred compositions of the present invention comprise fluorochemical emulsions that further incorporate at least one neuroprotective bioactive agent. Additional embodiments include oxygen carriers derived from human, animal, plant, or recombinant hemoglobin.

That is, the present invention further provides compositions comprising a synthetic oxygen carrier in a physiologically acceptable carrier, wherein the synthetic oxygen carrier comprises submicron sized particles capable of passing through emboli-obstructed blood vessels.

It should be understood that both the foregoing general description and the following detailed description are exemplary and explanatory only and are not restrictive of the invention as claimed. The accompanying drawings, which are incorporated in and constitute a part of the specification, illustrate various embodiments of the invention and, together with the description, serve to explain the principles of the invention.

DETAILED DESCRIPTION OF THE INVENTION

A. Overview of the Invention

The present invention provides methods of treating a mammal suffering from full or partial occlusion of a blood vessel, and therefore having ischemia and hypoxia in a tissue that depends on the blocked vessel for blood and oxygen, by administering intravenously a synthetic oxygen carrier. Preferably, the occlusion is the result of solid emboli comprising a naturally occurring structure such as a blood clot or lipid. In other embodiments the present invention comprises a method for imparting neuroprotection to a mammal through the administration of a synthetic oxygen carrier that may ameliorate effects associated with cerebral ischemia or hypoxia. Still other embodiments of the present invention comprise the administration of bioactive agents using a synthetic oxygen carrier. Preferably the bioactive agent is neuroprotective in nature and the oxygen carrier is a fluorochemical emulsion. Still other embodiments of the invention comprise the chronic or long-term administration of a synthetic oxygen carrier to ameliorate effects associated with ischemic or hypoxic conditions.

By "oxygen carrier" is meant a compound capable of transporting oxygen and other gases, although those other gases may not be explicitly stated when referring to the carrier. By "synthetic" is meant a compound that is chemically synthesized (e.g., fluorocarbons) or isolated and purified from a naturally occurring or biologically based source (e.g. hemoglobin purified from human, animal, plant, bacterial or other sources). By "solid emboli" is meant a constriction or occlusion of a blood vessel by a naturally occurring structure such as a blood clot, plaque particle, lipid droplets, cellular debris or dissection of the intimal lining of a blood vessel such as resulting from a mechanical procedure, such as occurs during balloon inflation in angioplasty procedures. The synthetic oxygen carrier used in the method of the present invention is preferably of sufficiently small size to continue to flow through the occluded vessel, unlike the whole red blood cells that are blocked, and therefore can promote gaseous exchange (e.g., oxygen delivery and removal of $CO_2$) in the ischemic tissue during the time before the occlusion is removed. The oxygen carrier may be delivered in a pharmaceutically acceptable carrier and preferably uses preparations which have a limited intravascular half-life (blood substitutes) that do not cause adverse hemodynamic effects. Preferred oxygen carriers include fluorocarbon emulsions, more preferably perfluorocarbon emulsions, a cellular Hb solutions and known crystalloid compositions and colloid compositions that are typically used as blood substitutes (i.e., compositions used to maintain a patient's normal blood volume and to increase cardiac output). Such oxygen carriers and blood substitutes are known in the art.

Suitable perfluorocarbons are biologically and biochemically inert compounds made of carbon and fluorine that dissolve oxygen and carbon dioxide and have a half-life of several hours in the body. Preferably, the perfluorocarbon oxygen carrier is administered as an emulsion having sufficiently small particles of perfluorocarbon suspended in an aqueous phase that the particles can pass by emboli in blood vessels, particularly in capillaries. That is, the submicron size of perfluorocarbon emulsions permits the oxygen carrier to perfuse the microcirculation of capillaries, including situations when vasoconstriction or partial occlusion prevents red blood cells from passing through the vessels, thus allowing the perfluorocarbon particles to perfuse the hypoxic tissue and provide some additional delivery of oxygen and removal of carbon dioxide. In the case of complete vessel occlusion, the small perfluorocarbon particles are still capable of perfusing through any partially patent collateral vessels to minimize the size of the hypoxic zone (i.e., the penumbra or region around the area of severe infarct, where the tissue is still viable but at risk of further injury if oxygen flow is not restored quickly). Other synthetic oxygen carriers that do not rely on submicron particle size of an emulsion, but that are also capable of perfusing partially occluded or collateral vessels are also contemplated by the present invention.

In addition to carrying oxygen, the synthetic oxygen carrier can also maintain or enhance the circulation of other dissolved gases (e.g., nitric oxide), and remove unwanted gases (e.g., $CO_2$ or $N_2$). Preferably, the oxygen carrier used is capable of removing or neutralizing free radicals generated at sites where ischemia or localized tissue hypoxia may be occurring, thereby ameliorating any inflammatory process and reperfusion injury that may otherwise occur when the blood supply is restored to the tissue.

The synthetic oxygen carrier can also serve as a means of delivering therapeutic drugs as an adjunct to the therapeutic oxygen delivery. For example, streptokinase or tPA can be delivered to the emboli, neuroprotectants can be delivered to neural tissue affected by the obstruction and anti-inflammatory agents may be delivered to an ischemic area to prevent further damage. Preferably, a perfluorocarbon emulsion is used to deliver physiologically acceptable amounts of the therapeutic drugs using well-known clinical protocols. Neuroprotectants that include 2-aminobenzothiazole derivatives, such as those disclosed in PCT International Application No. WO 97/15306, nerve growth factor (NGF), known physiologically active neuropeptides, or other anti-hypoxic drugs such as those disclosed in U.S. Pat. No.

4,861,785, can be added to the synthetic oxygen carrier composition for delivery of the tissue downstream of the blocked vessels. Other therapeutics suitable for delivery to the ischemic or hypoxic tissue using the synthetic oxygen carrier, preferably a perfluorocarbon emulsion, include neuropeptides, antagonists (i.e. NMDA, calcium, AMPA, adenosine, glycine or glutamate), acetyl-l-carnitine, free radical scavengers, sulfonylureas, calpastatin, inhibitors (cholinesterase, nitric oxide synthase, protein kinase C), NSAIDs, neurotrophic factors, vasodilators, antioxidants and combinations thereof.

Although the method of the present invention is generally contemplated as a treatment for hypoxic or ischemic tissue that has resulted from occlusions of vessels that have already occurred (i.e., when a patient presents with symptoms of occlusion), it can also be used prophylactically when the potential for occlusion resulting from solid emboli in the circulation is sufficiently high. For example, the method may be used during vascular, neural surgery and cardiac surgery in which solid emboli may be produced from atheromatous plaque particles that dislodge and move through the circulatory system, lodging in other atherosclerotic blood vessels. Moreover, the method is also contemplated to use as a post-surgical procedure for vascular, neurosurgery and cardiac surgery in atherosclerotic patients, even if occlusion resulting from dislodged plaque particles has not been clinically detected. Further, the disclosed methods may also be used to treat chronic or long term conditions through the administration of an oxygen carrier over a sustained period of weeks or months.

Although not wishing to be bound to any particular mechanism, it is believed that use of perfluorocarbons as oxygen carriers ameliorate ischemic damage due to solid emboli by providing oxygen to the tissue, either by passing around the occlusion or by increasing the gas exchange in collateral vessels to minimize the hypoxic zone, and by other anti-inflammatory properties associated with the perfluorocarbon compositions. Neat perfluorocarbons, particularly perfluoron, have been found to possess anti-inflammatory properties by affecting the cell membranes of white blood cells, thus preventing them from sticking to injured tissue or the occlusion. It is believed that the fluorochemical emulsions disclosed herein possess the same beneficial characteristics. For example, the methods of the present invention may prevent activated neutrophils from adhering to clotted fibrinogen. By minimizing the number of white blood cells that accumulate around the injured ischemic tissue, the cycle of progressively worsening localized inflammation is attenuated or interrupted, thereby preventing further injury to the hypoxic or surrounding tissue and allowing the tissue to heal. The ability of the perfluorocarbon composition to transport or inactivate reactive and toxic free radicals away from the site of injury, despite the occlusion, lowers the local concentration of these toxic chemicals in the hypoxic tissue, thus preventing progression of the inflammatory injury.

B. Materials

A large number of materials suitable for use in the present invention are already known in the art. Without limiting the scope of the invention, certain representative materials are discussed below.

Several compositions have been proposed or demonstrated to function as intravenous oxygen carriers. These include fluorocarbon emulsions, including but not limited to perfluorocarbon emulsions. Such emulsions are typically fluorocarbon-in-water emulsions having a discontinuous fluorocarbon phase and a continuous aqueous phase. The emulsions typically include emulsifying agents and osmotic agents, together with buffers and electrolytes.

The fluorocarbon emulsion may be selected from a wide range of suitable emulsions. Preferably, a fluorocarbon-in-water emulsion having a preferred fluorocarbon concentration of about 5% to about 125% weight per volume (w/v) is used. As used throughout, concentrations defined as "w/v" are understood to represent grams/dl, and "% weight per volume" are understood to represent grams/100 ml.

Fluorocarbons or fluorochemicals (used interchangeably herein) are fluorine substituted hydrocarbons that have been used in medical applications as imaging agents and as blood substitutes. U.S. Pat. No. 3,975,512 to Long discloses fluorocarbons, including brominated perfluorocarbons, used as a contrast enhancement medium in radiological imaging. Brominated fluorocarbons and other fluorocarbons are known to be safe, biocompatible substances when appropriately used in medical applications.

It is also known that gases in general, and particularly oxygen, are highly soluble in some fluorocarbons which has been exploited in development of blood substitutes comprising emulsified fluorocarbons. For a review of development of fluorocarbons as blood substitutes, see "Reassessment of Criteria for the Selection of Perfluorochemicals for Second-Generation Blood Substitutes: Analysis of Structure/Property Relationship" by Jean G. Riess, *Artificial Organs* 8:34–56, (1984) and see also Keipert, P E "Perfluorochemical Emulsions-Future Alternatives to Transfusion" *Blood Substitutes: Principles, Methods, Products and Clinical Trials*. Chang TMS (ed.) Karger Landes Bioscience Publishers, Basel (1997) pgs. 127–156.

In a preferred embodiment, the fluorocarbon is a perfluorocarbon or substituted perfluorocarbon. Fluorocarbon molecules used in these emulsions may have various structures, including straight or branched chain or cyclic structures, as described in Riess, J., *Artificial Organs* 8(1):44–56 (1984). These molecules may also have s degree of unsaturation, and may also contain bromine or hydrogen atoms, or may be amine derivatives. The fluorocarbons may be present in the emulsion in any useful concentration, but usually range from about 5% to 125% w/v.

Although concentrations as low as 5% w/v are contemplated, in a preferred embodiment the concentrations are at least about 25% or 30%, preferably at least about 40%, 50%, 55%, 60%, 75% or 80% w/v. Emulsions of about 60%, 85%, 90%, and 100% are particularly preferred, as are emulsions comprising perfluorooctyl bromide. Preferred fluorocarbon emulsion formulations include those disclosed in U.S. Pat. Nos. 4,865,836, 4,987,154, and 4,927,623, 6,628,930 and 5,635,538, which are hereby incorporated by reference.

There are a number of fluorocarbons that are contemplated for use in the present invention. These fluorocarbons include bis(F-alkyl) ethanes such as $C_4F_9CH$—$CH_4CF_9$ (sometimes designated "F-44E"), i-$C_3F_9CH$—$CHC_6F_{13}$ ("F-i36E"), and $C_6F_{13}CH$—$CHC_6F_{13}$ ("F-66E"); cyclic fluorocarbons, such as $C_{10}F_{18}$ ("F-decalin",) "perfluorodecalin" or "FDC"), F-adamantane ("FA"), F-methyladamantane ("FMA"), F-1,3-dimethyladamantane ("FDMA"), F-di- or F-trimethylbicyclo[3,3,1]nonane ("nonane"); perfluorinated amines, such as F-tripropylamine ("FTPA") and F-tributylamine ("FTBA"), F-4methyloctahydroquinolizine ("FMOQ"), F-n-methyldecahydroisoquinoline ("FMIQ"), F-n-methyldecahydroquinoline ("FHQ"), F-n- cyclohexylpurrolidine ("FCHP") and F-2-butyltetrahydrofuran ("FC-75" or "RM101").

Other suitable fluorocarbons may be selected from brominated perfluorocarbons, such as 1-bromo-heptadecafluoro-octane ($C_8F_{17}Br$, sometimes known as perfluorooctylbromide, "PFOB", or "perfluoron"), 1-bromopenta-decafluoroheptane ($C_7F_{15}Br$), and 1-bromotridecafluorohexane ($C_6F_{13}Br$, sometimes known as perfluorohexylbromide or "PFHB"). Other brominated fluorocarbons are disclosed in U.S. Pat. No. 3,975,512 to Long. Also contemplated are fluorocarbons having nonfluorine substituents, such as perfluorooctyl chloride, dichlorofluorooctane, perfluorooctyl hydride, and similar compounds having different numbers of carbon atoms (e.g., 6–12 carbons).

Additional fluorocarbons contemplated in accordance with this invention include perfluoroalkylated ethers or polyethers, such as $(CF_3)_2CFO(CF_2CF_2)_2OCF(CF_3)_2$, $(CF_3)_2CFO\text{—}(CF_2CF_2)_3OCF(CF_3)$, $(CF_3)CFO(CF_2CF_2)F$, $(CF_3)_2CFO(CF_2CF_2)_2F$, $(C_6F_{13})_2O$. Further, fluorocarbon-hydrocarbon compounds, such as, for example compounds having the general formula $C_nF_{2n+1}\text{—}C_{n'}F_{2n'+1}$, $C_nF_{2n+1}OC_{n'}F_{2n'+1}$, or $C_nF_{2n+1}CF\text{=}CHC_{n'F2n'+1}$, where n and n' are the same or different, and are from about 1 to about 10 (so long as the compound or a mixture containing the compound is a liquid at room temperature). Such compounds, for example, include $C_6F_{17}C_2H_5$ and $C_6F_{13}CH\text{=}CHC_6H_{13}$. It will be a that esters, thioethers, and other variously modified mixed fluorocarbon-hydrocarbon compounds are also encompassed within the broad definition of "fluorocarbon" materials suitable for use in the present invention. Mixtures of fluorocarbons are also contemplated for use in the discontinuous phase. Additional "fluorocarbons" not listed here, but having properties described herein that would lend themselves to use in vivo in accordance with the present invention, are further contemplated.

Emulsifying agents used in the emulsions of this invention may be anionic, cationic or non-ionic surfactants or combinations thereof, as are well known to those skilled in the art, or may be mixtures of synthetic compounds such as Pluronic F-68, a condensate of ethylene oxide with propylene glycol, as described in U.S. Pat. No. 4,073,879 to Long. Fluorosurfactants, such as those described by J. Riess et al. *Int'l Symposium on Blood Substiftutes*, Montreal (May, 1987), are also particularly suitable for use. Emulsifying agents may also be mixtures of the above described agents. Particularly suitable emulsifiers include natural amphipathic compounds such as phospholipids, particularly phosphatidylcholine, wherein combined hydrophilic and hydrophobic properties enable the molecule to interface with both aqueous and fluorocarbon systems, thereby forming emulsion droplets. There are various species of each class of phospholipids, such as the phospholipid cholines, comprising various pairings of saturated and unsaturated fatty acids in the glycerol structures. Phosphatidylcholine is an abundant natural material (lecithin) which may be purified from egg yolk, or produced synthetically (Avanti Polar Lipids, Pelham, Ala.). Phospholipid emulsifiers, particularly egg yolk phospholipid and lecithin, are particularly preferred.

Exemplary phospholipids useful in the disclosed stabilized preparations comprise egg phosphatidylcholine, dilauroylphosphatidylcholine, dioleylphosphatidylcholine, dipalmitoylphosphatidylcholine, disteroyl-phosphatidylcholine, short-chain phosphatidylcholines, phosphatidylethanolamine, dioleylphosphatidyl-ethanolamine, phosphatidylserine, phosphatidylglycerol, phosphatidylinositol, glycolipids, ganglioside GM1, sphingomyelin, phosphatidic acid, cardiolipin; lipids bearing polymer chains such as polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate. Due to their excellent biocompatibility characteristics, phospholipids and combinations of phospholipids and poloxamers are particularly suitable for use in the stabilized dispersions disclosed herein.

The phospholipid emulsifying agent is typically included in the range of from about 2 to 14% w/v, usually increasing the phospholipid concentration with increasing fluorocarbon concentration. In a preferred embodiment, the phospholipid comprises at least 2% w/v of the emulsion. The preferred amount for an emulsion comprising 75% w/v bromofluorocarbon is 2.5 to 5% w/v of phospholipid, and for an emulsion having 100% w/v bromofluorocarbon is 3.5 to 10% w/v of phospholipid.

In addition to the lipids discussed above, compatible nonionic detergents comprise: sorbitan esters including sorbitan trioleate (Span® 85), sorbitan sesquioleate, sorbitan monooleate, sorbitan monolaurate, polyoxyethylene (20) sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Other suitable nonionic detergents can be easily identified using McCutcheon's Emulsifiers and Detergents (McPublishing Co., Glen Rock, N.J.) which is incorporated herein in its entirety. Preferred block copolymers include diblock and triblock copolymers of polyoxyethylene and polyoxypropylene, including poloxamer 188 (Pluronic® F68), poloxamer 407 (Pluronic® F-127), and poloxamer 338. Ionic surfactants such as sodium sulfosuccinate, and fatty acid soaps may also be utilized. It will be appreciated that these surfactants may be used alone, in combination with one another or in combination with the lipids discussed above.

Besides the aforementioned surfactants, cationic surfactants or lipids may be preferable in embodiments comprising delivery of nucleic material such as RNA or DNA. Examples of suitable cationic lipids include: DOTMA, N-[1-(2,3-dioleyloxy)propyl]-N,N,N-trimethylammonium chloride; DOTAP, 1,2-dioleyloxy-3-(trimethylammonio)propane; and DOTB, 1,2-dioleyl-3-(4'-trimethylammonio) butanoyl-sn-glycerol. Polycationic amino acids such as polylysine, and polyarginine are also contemplated.

Those skilled in the art will further appreciate that a wide range of surfactants may optionally be used in conjunction with the present invention. Moreover, the optimum surfactant or combination thereof for a given application can readily be determined by empirical studies that do not require undue experimentation.

In any event, emulsification requires large amounts of energy to convert a twophase immiscible system into a suspension of discontinuous small droplets of hydrophobic fluid in an aqueous continuous phase. Fluorocarbon emulsification may be carried out generally by either of two general processes that provide energy to the system to break up the fluorocarbon volume into small droplets. In sonication emulsification, a probe is inserted into the mixture of fluorocarbon, emulsifier, and aqueous phase, and bursts of energy are released from the tip of the probe. In mechanical emulsification, such as the process performed by a MICROFLUIDIZER apparatus (Microfluidics, Newton, MA 02164), streams of the mixed emulsion components are directed through the apparatus at high velocity and under high pressure (e.g. 15,000 psi), and the mechanical stress applied to the fluid produces high shear force or cavitation that produces the emulsion.

For example, in selected embodiments an oilinwater emulsion may be formed in an appropriate vessel. As discussed above, the oil employed is preferably a fluorocarbon (e.g., perfluorooctyl bromide, perfluorodecalin) which is emulsified using a surfactant such as a long chain saturated phospholipid. In such embodiments, the selected amount of phospholipid may be homogenized in a predetermined volume of hot distilled water (e.g., 60° C.) using a suitable high shear mechanical mixer (e.g., Ultra-Turrax model T-25 mixer) at 8000 rpm for 2 to 5 minutes. Typically, an appropriate amount of fluorocarbon (depending on the selected final w/v) is added slowly to the dispersed surfactant solution while mixing. The resulting perfluorocarbon in water emulsion is then processed using a high pressure homogenizer to reduce the particle size. Typically the emulsion is processed at 12,000 to 18,000 psi for 5 discrete passes and kept at 50 to 80° C.

The aqueous phase of the emulsion may have components dissolved therein which give the emulsion desirable properties. For example, it may comprise an osmotic agent to bring the emulsion to physiological isotonicity. The osmotic agent may be sodium chloride, or it may be a polyhydroxyl compound, such as, for example, a sugar or mannitol. The aqueous phase may also contain soluble buffering agents.

The lipid phase of the emulsion may also have components dissolved therein. For example, a phosphatidyl choline emulsifier may have glycerol, phosphatidyl glycerol, other phospholipids or cholesterol admixed, and further contain an antioxidant substance, such as a tocopherol, to protect against lipid oxidation.

Several fluorocarbon emulsions have been produced commercially for use as intravascular oxygen carriers. These include a mixed decalin emulsion formerly sold by Alpha Therapeutics Corp., Los Angeles, Calif., under the trademark FLUOSUL. and perfluoron-based emulsions being developed by Alliance Pharmaceutical Corp. of San Diego, Calif., under the trademark OXYGENT™. It will be appreciated that each of the foregoing compositions are particularly compatible with the methods of the present invention.

Hemoglobin compositions contemplated for use in the present invention are well known. Such compositions are disclosed, for example, in the following U.S. Patents, which are hereby incorporated by reference: U.S. Pat. Nos. 4,911,929; 4,861,867:4,857,636; 4,777,244; 4,698,387; 4,600,531; 4,526,715; 4,473,494; and 4,301,144.

Plasma expanders may be optionally used together with the synthetic oxygen carrier. Various materials have been used successfully as plasma expanders which are administered using well known methods to maintain the patient's blood volume in the normal range and to encourage the increase in cardiac output where insufficient blood volume may be a factor in the condition being treated (e.g., during or following surgery where risk of developing emboli is increased). These include the well-known categories of crystalloid compositions (e.g., Ringers-lactate and saline (0.9%), both from Baxter Healthcare Corp., Deerfield, Ill.) and colloid compositions. Physiologically acceptable crystalloid compositions comprise aqueous solutions or suspensions of inorganic and organic components normally found in blood or derived from salts that are compatible with human physiology, osmolarity agents and an optionally an oxygen carrier (i.e., a hemoglobin substitute). The organic components include, for example, glucose (90 mEq/L) and amino acids (30 mEq/L or amino acid analogs such as those disclosed in U.S. Pat. No. 5,114,932. The inorganic components are included in physiological concentrations, such as for example, sodium (142 mEq/L), chloride (103 mEq/L), potassium (4 mEq/l), calcium (5 mEq/L), magnesium (3 mEq/L), bicarbonate (28 mEq/l), phosphate (4 mEq/L), sulfate (1 mEq/L). The osmolarity agents include disaccharides, such as maltose, lactose, sucrose or cellobiose, to achieve an osmolarity of about 400 to about 800 milliosmoles/L. The oxygen carriers are fluorocarbons, such as those described above, or hemoglobin substitutes, including for example α, β and γ cyclodextrins, such as those described in U.S. Pat. No. 5,114,392. Buffering agents (acids, bases or buffers) sufficient to adjust the pH of the solution to physiologically acceptable levels may also be included.

Known and commercially available colloid compositions include: (1) modified fluid gelatins (such as PLASMA-GEL™ from R. Bellon Lab. (Neuillysur Seine, France), GELIFUNDOL™ from Biotest (Frankfurt, Germany), GELOFUSINE™ from Braun (Melsungen, Germany) and HAEMACEL™ from Hoechst-Roussel Pharmaceutical Inc. (Sommerville, N.J.)); (2) dextran solutions, such as dextran-70 solution or MACRODEX™ and dextran-40 solution or RHEOMACRODEX™, both from Pharmacia (Piscataway, N.J.); (3) albumin solutions, such as ALBUTEIN™ from Alpha Therapeutics (Los Angeles, Calif.) and 5% human serum albumin from Abbott Labs (North Chicago, Ill.); and (4) starch solutions, such as hydroxyethylstarch or hetastarch solution, available as HAES™ from Fresenius (Hamburg, Germany) and HESPAN™ from DuPont (Willmington, Del.).

Known plasma expanders can be used separately but in conjunction with, or as a carrier for, the oxygen carrier and/or additional bioactive agents used in accordance with the methods of the present invention.

C. Procedures

Following diagnosis of a blood vessel occlusion using standard clinical methods, a patient suspected of having tissue hypoxia due to localized ischemia resulting from the occlusion is administered a synthetic oxygen carrier, such as any of the compounds described above. Preferably, the synthetic oxygen carrier is a perfluorocarbon-in-water emulsion that contains a discontinuous perfluorocarbon phase of sufficiently small size to enter a blood vessel, particularly a capillary, and pass by the embolus occluding the vessel. Synthetic oxygen carriers with compatible intravascular persistence for the dosage administered can readily be determined by those skilled in the art using standard clinical procedures. If needed to maintain normal hemodynamics, the procedure may include limited removal of a portion of the patient's blood to accommodate the volume of synthetic oxygen carrier introduced into the patient.

Using standard clinical procedures, sufficient synthetic oxygen carrier may be administered intravenously in a fluid to permit regulation of cardiac output in order to maintain oxygen delivery at a level at least approximately equivalent to normal physiological levels. This intravenous fluid may include an oxygen carrier other than red blood cells, preferably a biocompatible fluorocarbon emulsion of the type discussed above, or known hemoglobin-containing blood substitutes as the oxygen carrier. The intravenous fluid may also include a plasma expander, such as a colloid or crystalloid. In addition to administering the disclosed compositions intravascularly, it will be appreciated that, in selected cases (e.g. drug delivery), the emulsions of the present invention may be administered intramuscularly, intraperitoneally, orally or topically to provide oxygen, and/or any incorporated bioactive agent to desired site. Such methods of administration may be applicable, for example, during ocular surgery.

When used intravascularly, the volume of administered emulsion may vary based on clinical parameters. That is, while it will depend ultimately upon the duration and other particulars of the therapeutic regimen, the volume of intravenous fluid administered to the patient may be at least about equal to 0.1%, preferably at least about 1% to 20%, and more preferably up to about 20–30% of the patient's normal blood volume, which can readily be determined by the patient's weight and physiologic condition. Alternatively, the volume of intravenous fluid administered to the patient is adequate to replace any blood removed from the patient either by injury or to reduce the patient's blood volume as discussed above. Of course, when the invention comprises treatment of a condition involving the chronic or long term administration of an oxygen carrier, the individual doses may be much smaller. In such cases, the oxygen carrier may be administered in a relatively dilute form in a continuous infusion or repeatedly administered in a more concentrated form intermittently or periodically over a period of days, weeks, months or even years.

In selected embodiments of the invention involving relatively short term therapeutic regimens, the intravenous fluid may comprise both plasma expander and oxygen carrier. The volume ratio of expander to an oxygen carrier can range from 1:1 to at least 10:1, depending on whether the fluid is a crystalloid or a colloid, and on the composition of the oxygen carrier, the concentration of the oxygen carrier, $PO_2$ and cardiac output. These ranges are most desirable when using a high concentration fluorocarbon emulsion, having at least about 40% w/v, preferably at least about 50% w/v, and more preferably about 60% w/v fluorocarbon (or up to 90% w/v for situations where small volume doses are desirable). Preferably, a major portion of the intravenous fluid is a plasma expander and a minor portion is the oxygen carrier.

In a preferred single dosage embodiment, where a fluorocarbon emulsion such as perfluoron-based emulsion is the oxygen carrier, the amount of perfluorocarbon administered to the patient, based on the patient's weight, is from about 0.5 g PFC/kg to about 10 g PFC/kg, preferably about 1 to 5 g PFC/kg. Simple calculation provides the preferred volume of emulsion when different concentrations of fluorocarbon are used.

After or simultaneously with administration of the oxygen carrier, a breathing gas enriched in oxygen may be administered. In such embodiments the oxygen concentration is preferably at least 50–60%, and more preferably up to 100%. The effects of the enriched breathing gas, the oxygen carrier, and the dissolved oxygen in the aqueous portion of the circulating intravascular fluid all combine to supply enhanced levels of oxygen to the patient, particularly to the hypoxic or ischemic tissue downstream from the blood vessel occlusion. The collective contributions of these factors to oxygen delivery in the patient are known and have been described by the Fick equation which is discussed in U.S. Pat. No. 5,451,205 incorporated herein by reference.

In preferred embodiments of the present invention the patient may be treated for a solid occlusion using standard clinical methods as determined by the treating physician (e.g., surgical bypass of the blocked vessel, removal or dissolving the embolus by mechanical and/or enzymatic means). The intravenous oxygen carrier can be used to provide oxygen to hypoxic tissue having blood supply blocked by such emboli and may be prior to, during and/or after such treatment to remove the occlusion. Because of the urgency of treating hypoxic or ischemic tissue, particularly heart or nervous tissue, to ameliorate tissue damage resulting from the emboli, treatment with intravenous oxygen carrier is preferably begun as soon as occlusion is detected or suspected.

More particularly, it is contemplated that this type of acute treatment involves intravenous administration of a synthetic oxygen carrier during the first 5 min to hour of therapy, and may continue for about 24 hr to about seven days, depending on the patient's condition and additional treatment of the occlusion. Preferably, about 0.50 to 1 ml/kg, up to about 50 ml/kg of a perfluorocarbon emulsion is administered by injection or infusion during the first hour of therapy. Then, during the next day to 7 days, additional volumes (e.g., about 2 ml/kg to about 10 ml/kg) of a perfluorocarbon emulsion can be administered depending on the additional surgical or nonsurgical treatment given, as determined by the treating physician. That is, as long as the physician determines or suspects that hypoxia or ischemia is resulting from a solid occlusion of a blood vessel, administration of the synthetic oxygen carrier is continued until the physician has determined that the vessel is no longer occluded.

Conversely, as indicated above, the present invention further comprises the chronic or long term treatment of ischemic or hypoxic conditions. As will be appreciated a "chronic or long term condition" is one which lasts for a relatively long time or is marked by frequent recurrence. For the purposes of the present disclosure, a chronic or long term condition is one in which the patient will benefit from a therapeutic regimen comprising a treatment period of longer than one week. That is, in the present invention chronic or long term conditions will be those which benefit from the administration of oxygen carrier for more than one week. Accordingly, in those embodiments directed to the treatment of such conditions the selected oxygen carrier may be administered intermittently, periodically or continuously over a period of days, weeks, months or even years. These conditions may be contrasted with more acute conditions (such as a heart attack or stroke) that benefit from immediate and substantial treatments such as those described immediately above.

When administered continuously or relatively often, the absolute amount of oxygen carrier per dose is preferably reduced below the amounts appropriate for the acute treatments described above. In exemplary embodiments the oxygen carrier may be administered once a day or once a week for as long as necessary to ameliorate or retard the effects of the ischemic or hypoxic conditions. In other embodiments the oxygen carrier may be administered intermittently as needed (i.e. as determined by clinical indicators) for as long as necessary. While such chronic therapeutic regimens can be used in conjunction with any hypoxic or ischemic condition such as atherosclerosis, they may be particularly effective for treating neurodegenerative disorders. For example, the methods disclosed herein may preferably be used to treat chronic neurodegenerative conditions such as those arising from intermittent strokes, Alzheimer's disease, Parkinson's disease or epilepsy.

As alluded to above, drugs can be simultaneously delivered with the synthetic oxygen carrier treatment. That is, drugs can be administered separate from, but simultaneously with, administration of the oxygen carrier, or a combination of the synthetic oxygen carrier and therapeutic drugs may be administered to treat hypoxia or ischemia. Moreover, at different stages of treatment or for treatment of hypoxia in particular tissues, different combinations of drugs and oxygen carrier may be used. For example, during the initial therapy the oxygen carrier composition may also include a drug to promote dissolving the solid obstruction such as streptokinase or tPA. During this initial treatment or following the initial therapy, the oxygen carrier composition may include a drug that is specifically directed to the hypoxic tissue such as a neuroprotective agent for an occlusion of a vessel that supplies blood to CNS tissue. Preferably, the oxygen carrier is fluorocarbon, and more preferably is a perfluorocarbon emulsion.

More generally, as alluded to above, compatible bioactive agents may comprise antibiotics, antivirals, anti-inflammatories, steroids, antihistaminics, histamine antagonists, leukotriene inhibitors or antagonists, anticholinergics, antineoplastics, anesthetics, enzymes, cardiovascular agents, genetic material including DNA and RNA, viral vectors, immunoactne agents, imaging agents, vaccines, immunosuppressive agents, peptides, proteins and combinations thereof. Particularly preferred bioactive agents comprise antiinflammatories, neuroprotectants and vasodilators. For systemic delivery (e.g. for the treatment of autoimmune diseases such as diabetes or multiple sclerosis), peptides and proteins are particularly preferred.

Exemplary medicaments or bioactive agents may be selected from, for example, analgesics, e.g. codeine, dihydromorphine, ergotamine, fentanyl, or morphine; anginal preparations, e.g. diltiazem; mast cell inhibitors, e.g. cromolyn sodium; antiinfectives, e.g. cephalosporins, macrolides, quinolines, penicillins, streptomycin, sulphonamides, tetracyclines and pentamidine; antihistamines, e.g. methapyrilene; anti-inflammatories, e.g. fluticasone propionate, beclomethasone dipropionate, flunisolide, budesonide, tripedane, cortisone, prednisone, predrisilone, dexamethasone, betamethasone, or triamcinolone acetonide; antitussives, e.g. noscapine; bronchodilators, e.g. ephedrine, adrenaline, fenoterol, formoterol, isoprenaline, metaproterenol, salbutamol, albuterol, salmeterol, terbutaline; diuretics, e.g. amiloride; anticholinergics, e.g. ipatropium, atropine, or oxitropium; lung surfactants e.g. Surfaxin, Exosurf, Survanta; xanthines, e.g. aminophylline, theophylline, caffeine; therapeutic proteins and peptides, e.g. DNAse, insulin, glucagon, T-cell receptor agonists or antagonists, LHRH, nafarelin, goserelin, leuprolide, interferon, rhu IL-1 receptor, macrophage activation factors such as lymphokines and muramyl dipeptides, opioid peptides and neuropeptides such as enkaphalins, endorphins, renin inhibitors, cholecystokinins, growth hormones, leukotriene inhibitors, α-antitrypsin, and the like. In addition, bioactive agents that comprise an RNA or DNA sequence, particularly those useful for gene therapy, genetic vaccination, genetic tolerization or antisense applications, may be incorporated in the disclosed dispersions as described herein. Representative DNA plasmids include, but are not limited to pCMVβ (available from Genzyme Corp, Framington, Mass.) and pCMV-β-gal (a CMV promotor linked to the *E. coli* Lac-Z gene, which codes for the enzyme β-galactosidase).

It will further be appreciated that formulations according to the invention may, if desired, contain a combination of two or more bioactive agents. These individual agents could be added to the emulsion in any desired proportion and placed in delivery systems as described herein.

Based on the foregoing, it will be appreciated by those skilled in the art that a wide variety of bioactive agents may be incorporated in the disclosed stabilized dispersions. Accordingly, the list of preferred bioactive agents above is exemplary only and not intended to be limiting. It will also be appreciated by those skilled in the art that, the proper amount of bioactive agent and the timing of the dosages may be determined for the formulations in accordance with already-existing information and without undue experimentation.

The methods of this invention are useful for preventing or treating hypoxic or ischemic conditions that result from solid emboli that result from naturally occurring disease conditions such as atherosclerosis, or that result from dissection f intimal mining of a blood vessel as can occur following a mechanical procedure such as catheterization or percutaneous angioplasty. The method of this invention is also useful for amelioration of tissue damage that occurs when ischemic or hypoxic conditions due to solid emboli are detected or suspected, but before treatment can be completed to remove the emboli. This can be especially important in preventing memory loss or confusion or other neurologic complications and adverse outcomes associated with cerebral emboli or stroke, or for preventing cardiac muscle damage associated with AMI or low-flow myocardial ischemia. The method of the present invention are also useful for delivery of therapeutic drugs as an adjunct for ameliorating tissue damage resulting from ischemia.

Unless defined otherwise, all scientific and technical terms used herein have the same meaning as commonly understood by those skilled in the relevant art. General definitions of many of the terms used herein are provided in *Dorland's Illustrated Medical Dictionary*, 27th ed. (W. A. Bodand, 1988, W. B. Saunders Co., Philadelphia, Pa.). Unless mentioned otherwise, the techniques employed or contemplated herein are standard methodologies well known to one of ordinary skill in the art. The examples of embodiments are for illustration only.

The invention can be better understood by way of the following examples which are representative of the preferred embodiments, but which are not to be construed as limiting the scope of the invention.

EXAMPLE 1

Exemplary Perfluoron Emulsion

A perfluorocarbon emulsion suitable for use is a 90% (w/v) perfluoron emulsion having the following formula prepared and sterilized using standard methods known to those skilled in the art:

| Component | Percent (w/v) |
|---|---|
| Perflubron | 90.000 |
| Egg Yolk Phospholipid | 4.000 |
| $NaH_2PO_4.H_2O$, USP | 0.052 |
| $Na_2HPO_4.7H_2O$, USP | 0.355 |
| NaCl, USP | 0.280 |
| EDTA, USP | 0.020 |
| d-α-tocopherol, USP | 0.002 |
| Water for injection | 48.400. |

Those skilled in the art will appreciate that this emulsion may be used in conjunction with the teachings herein to prevent or treat tissue hypoxia or ischemia, provide neuroprotection or retard neurodegeneration, provide for chronic or long-term therapeutic regimens and mediate the delivery of bioactive agents.

It should be apparent from the foregoing description of the invention that various agents may be substituted in the examples to give similar results, so long as the oxygen carrier forms sufficiently small droplets that can circulate around emboli that prevent movement of red blood cells through a blood vessel. Accordingly, the invention may be embodied in other specific forms without departing from it in spirit to be considered in all respects only as illustrative and not as restrictive. The scope of the invention is, therefore, indicated by the appended claims rather than by the foregoing description. All modifications which come within the meaning and range of the lawful equivalency of the claims are to be embraced within their scope.

We claim:

1. A synthetic oxygen carrier for in vivo use comprising a fluorocarbon emulsion having a continuous and discontinuous phase, wherein the emulsion is combined in vivo with a neuroprotective compound for retarding neurodegeneration wherein the neuroprotective compound is located in the discontinuous phase of the fluorocarbon emulsion.

2. The synthetic oxygen carrier of claim 1, wherein the synthetic oxygen carrier is administered by intravenous injection or infusion.

3. The synthetic oxygen carrier of claim 1, wherein the fluorocarbon emulsion comprises a perfluorocarbon phase and an aqueous phase.

4. The synthetic oxygen carrier of claim 1, wherein the fluorocarbon emulsion further comprises an emulsifying agent, osmotic agent, buffer, electrolyte or combinations thereof.

5. The synthetic oxygen carrier of claim 1, wherein the fluorocarbon emulsion comprises a compound selected from the group consisting of a straight chain perfluorocarbon, branched chain perfluorocarbon, cyclic perfluorocarbon or combinations thereof.

6. The synthetic oxygen carrier of claim 1, further comprising administering a bioactive agent with the synthetic oxygen carrier.

7. The synthetic oxygen carrier of claim 1, wherein the neuroprotective compound is selected from the group consisting of a neuropeptide, a nerve growth factor and a 2-aminobenzothiazole derivative.

8. The synthetic oxygen carrier of claim 1, wherein the synthetic oxygen carrier is administered within one hour of therapy for symptoms associated with ischemia.

9. The synthetic oxygen carrier of claim 1, wherein the synthetic oxygen carrier is administered within 24 hours of therapy for symptoms associated with ischemia.

10. The synthetic oxygen carrier of claim 1, wherein the synthetic oxygen carrier is administered prior to a surgical procedure to remove emboli associated with ischemia.

11. The synthetic oxygen carrier of claim 1, wherein the synthetic oxygen carrier is administered during or after a surgical procedure to remove emboli associated with ischemia.

12. The synthetic oxygen carrier of claim 1, wherein the synthetic oxygen carrier is between about 1% to about 10% of an individual's normal blood volume.

* * * * *